(12) United States Patent
Skubitz et al.

(10) Patent No.: US 11,864,788 B2
(45) Date of Patent: Jan. 9, 2024

(54) METHODS AND TOOLS FOR CLEARING FOR EPIDURAL SPACE IN PREPARATION FOR MEDICAL LEAD IMPLANTATION

(71) Applicant: MEDTRONIC, INC., Minneapolis, MN (US)

(72) Inventors: Sean P. Skubitz, Forest Lake, MN (US); Christopher M. Boyd, Hudson, WI (US); Jonathan C. Sell, St. Paul, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 488 days.

(21) Appl. No.: 16/940,330

(22) Filed: Jul. 27, 2020

(65) Prior Publication Data
US 2020/0352589 A1 Nov. 12, 2020

Related U.S. Application Data

(62) Division of application No. 13/752,566, filed on Jan. 29, 2013, now Pat. No. 10,751,081.

(60) Provisional application No. 61/618,660, filed on Mar. 30, 2012.

(51) Int. Cl.
*A61B 17/3207* (2006.01)
*A61B 17/32* (2006.01)
*A61N 1/05* (2006.01)

(52) U.S. Cl.
CPC .. *A61B 17/3207* (2013.01); *A61B 17/320016* (2013.01); *A61N 1/0551* (2013.01); *A61B 2017/320044* (2013.01); *A61B 2017/320056* (2013.01)

(58) Field of Classification Search
CPC ........ A61B 17/3207; A61B 17/320016; A61B 2017/320044; A61B 2017/320056; A61N 1/0551
See application file for complete search history.

(56) References Cited

U.S. PATENT DOCUMENTS

| 5,522,819 | A | * | 6/1996 | Graves | A61B 17/221 606/113 |
| 2004/0210245 | A1 | * | 10/2004 | Erickson | A61B 17/3468 606/167 |
| 2005/0288758 | A1 | * | 12/2005 | Jones | A61B 17/3415 607/116 |
| 2007/0233222 | A1 | * | 10/2007 | Roeder | A61F 2/966 623/17.13 |

(Continued)

*Primary Examiner* — Richard G Louis
(74) *Attorney, Agent, or Firm* — WITHERS & KEYS, LLC

(57) ABSTRACT

An epidural space is cleared of fat and scar tissue in preparation for implantation of a medical lead by utilizing a clearing tool. The clearing tool has an outer body and an inner body present within a lumen of the outer body. The outer body may be malleable and have a pre-set deflection or may be flexible and achieve deflection when being inserted into the epidural space. Once in the epidural space, the inner body is extended distally from the lumen of the outer body such that a distal tip on the inner body extends further into the epidural space to provide clearing to the target site without requiring further ingress of the outer body. The inner body is retracted and the clearing tool is removed. The medical lead is then inserted through the window and cleared epidural space until reaching the target site.

5 Claims, 8 Drawing Sheets

(56) References Cited

U.S. PATENT DOCUMENTS

2009/0018507 A1* 1/2009 Schmitz ............ A61B 17/1757
604/164.04

* cited by examiner

METHODS AND TOOLS FOR CLEARING FOR EPIDURAL SPACE IN PREPARATION FOR MEDICAL LEAD IMPLANTATION

RELATED APPLICATIONS

This application is a divisional application of U.S. patent application Ser. No. 13/752,566, filed Jan. 29, 2013, which claims priority to U.S. Provisional Appl. No. 61/618,660, filed on Mar. 30, 2012, both of which are incorporated by reference herein.

TECHNICAL FIELD

Embodiments are related to the implantation of medical leads used for stimulation within the epidural space. More particularly, embodiments relate to methods and tools for clearing the epidural space in preparation for implantation of a medical lead.

BACKGROUND

Various medical conditions may call for therapeutic electrical stimulation within the epidural space of the spine. Therefore, medical leads capable of delivering stimulation signals are implanted within the epidural space. In some cases, it may be necessary to clear the epidural space as well as the entryway to the epidural space of fatty tissue, scar tissue, and the like in order to provide for easier ingress of the medical lead. This is particularly true for paddle leads that are implanted through a surgical procedure due to the relatively wide distal paddle on the medical lead.

Conventionally, a rigid plastic tool or a soft tool is inserted into the epidural space through a window created within the vertebral bone and associated ligaments. However, the rigid plastic tool presents multiple issues. A first issue is that the rigid plastic provides minimal deflection when entering the epidural space at an angle through the window and thus creates a potential pressure point along the dura of the spinal cord which can cause discomfort and potential paralysis. Another issue is that once in the epidural space, the rigid plastic tool often has less than adequate clearing ability. The soft plastic also presents multiple issues. Once inside the epidural space the soft plastic may deflect in an undesired direction. Additionally, the soft plastic may not have the stiffness to track in the ideal direction. This is particularly true as the width and length of the paddle continues to grow with newer versions of paddle leads where the increased paddle width increases the likelihood of snagging the blockages within the epidural space. Furthermore, the rigid plastic tool with minimal deflection cannot enter at a shallow enough angle to allow for adequate insertion distance needed to reach and clear the target stimulation site.

SUMMARY

Embodiments address issues such as these and others by providing methods for clearing the epidural space and implanting the medical lead and for related tools. Once the window is created, a clearing tool is inserted through the window and into the epidural space. The clearing tool has an inner body retracted into a lumen of an outer body. The outer body may be malleable and have a pre-set deflection for entering the epidural space or may be flexible so as to deflect as appropriate during entry to the epidural space. Once the distal end of the outer body is present within the epidural space, the inner body is extended distally out of the lumen to further extend through the epidural space. A distal tip on the inner body clears the epidural space as the inner body is being extended and then subsequently retracted back into the lumen. The clearing tool is removed and the medical lead is then inserted into the epidural space and to the target site.

Embodiments provide a method of implanting a medical lead within an epidural space that involves inserting a clearing tool through a window into the epidural space. The method further involves extending a distal end of an inner body distally from a distal end of a lumen of an outer body of the clearing tool and further into the epidural space to clear the epidural space, the inner body having a distal tip with a greater diameter than the inner body. Additionally, the method involves retracting the distal end of the inner body proximally into the outer body, removing the clearing tool through the window, and inserting the medical lead into the cleared epidural space.

Embodiments provide a clearing tool for clearing an epidural space in preparation for implantation of a medical lead within the epidural space. The clearing tool includes an outer body with a lumen having a distal end and a proximal end and an inner body within the lumen. The inner body is movable in an axial direction within the lumen relative to the outer body between an extended state and a retracted state. A proximal end of the inner body resides proximal to the proximal end of the outer body at least when the inner body is in the retracted state and a distal end of the inner body resides distal to the distal end of the outer body at least when the inner body is in the extended state. A distal tip is affixed to a distal end of the inner body and resides distally of the lumen at least when the inner body is in the extended state, the distal tip having a greater diameter than the inner body.

Embodiments also provide a method of clearing an epidural space in preparation for implantation of a medical lead within the epidural space. The method involves inserting a clearing tool through a window into the epidural space, the clearing tool including an inner body present within a lumen of an outer body. The method further involves extending a distal end of the inner body distally from a distal end of the lumen of the outer body of the clearing tool and further into the epidural space to clear the epidural space, the inner body having a distal tip with a greater diameter than the inner body. Additionally, the method involves retracting the distal end of the inner body proximally into the outer body and removing the clearing tool through the window prior to inserting the medical lead.

DETAILED DESCRIPTION

Embodiments provide methods and tools to clear the epidural space in preparation for implanting a medical lead such as a stimulation lead with a paddle on the distal end. The method involves inserting the clearing tool into the epidural space while an inner body is in a retracted state within a lumen of an outer body. The inner body is then extended distally from the lumen and farther into the epidural space and to the target site and then retracted proximally. The clearing tool is them removed, and upon removal of the clearing tool, the medical lead is then inserted to the target site within the cleared epidural space. The clearing tool may include a body that is malleable so that a deflection is pre-established for ease of ingress of the body into the epidural space, or alternatively the clearing tool may include a body that is flexible so as to deflect during entry.

Figure 1:
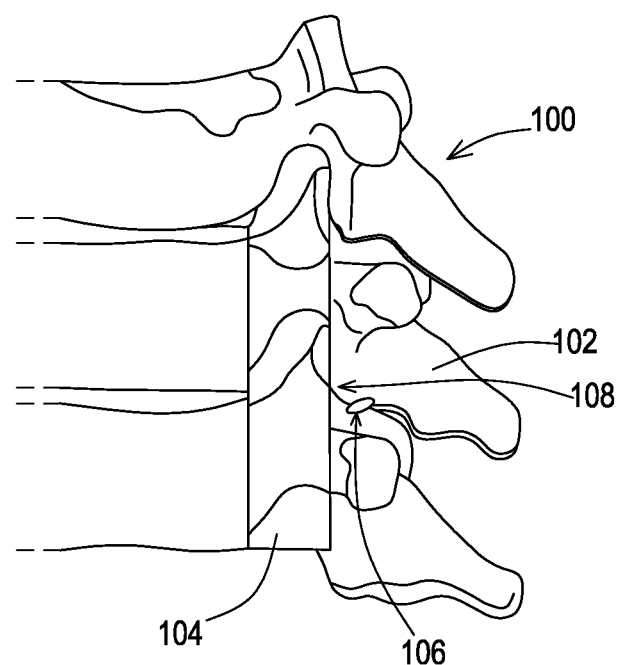
FIG. 1 shows a spine with a window created to access the epidural space.

FIGS. 1-6 illustrate a method of clearing the epidural space and implanting the medical lead within the cleared epidural space. FIG. 1 shows a spinal region 100 of a patient where the implantation of a medical lead is desired. Prior to clearing the epidural space 108, a surgeon has created a window 106 in the spinal region 100 in the conventional manner by cutting through any vertebral bone and ligaments that block entryway to the epidural space 108 that occurs between the dura 104 of the spinal cord and the inner surface of the vertebral bone 102.

Figure 2:
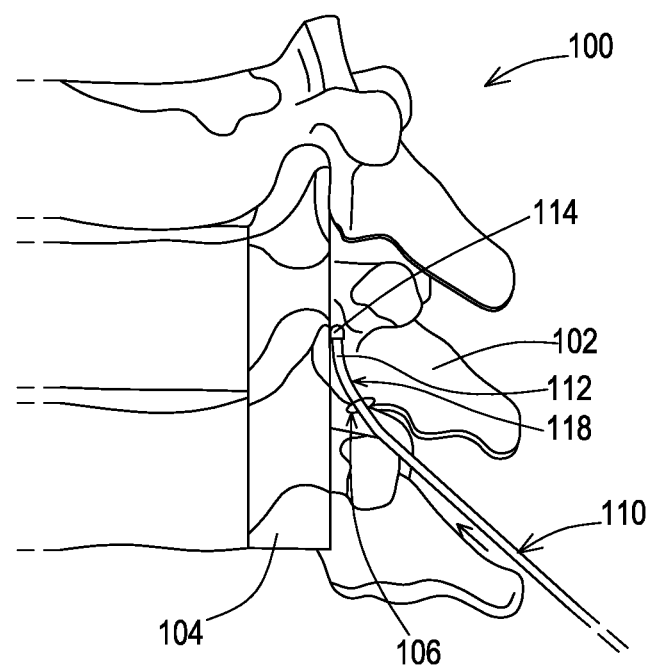
FIG. 2 shows an example of a clearing tool being inserted into the epidural space while in a retracted state.

FIG. 2 shows the insertion of the clearing tool 110 into the epidural space 108 by passing through the window 106 until the distal end of the clearing tool 110 becomes directed axially along the dura 104. As can be seen, an outer body 112 of the clearing tool 110 has deflected to achieve the alignment in the axial dimension of the dura 104. This deflection may be the result of a pre-formed deflection in the area 118 of the outer body 112 where the outer body 112 is malleable to ensure that the clearing tool 110 does not create undue pressure on the dura 104 when entering the epidural space 108. Alternatively, this deflection may occur as the clearing tool 110 is being inserted where the clearing tool 110 includes a flexible outer body 112.

During this insertion, the clearing tool 110 is in a retracted state where the distal tip 114 is retracted to a close proximity to the outer body 112. Thus, the length of the outer body 112 being inserted is significantly less than that necessary to reach the target site within the epidural space 108. Therefore, there is a reduced chance of creating undue pressure on the dura 104 during the insertion of the outer body 112.

Figure 3:
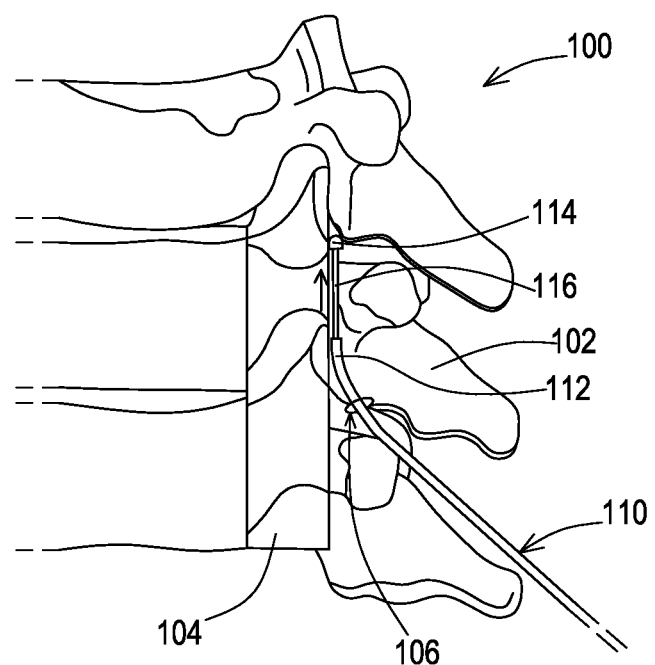
FIG. 3 shows the clearing tool transitioning to an extended state within the epidural space.

FIG. 3 shows an inner body 116 of the clearing tool 110 being extended distally from the outer body 112 in order to extend the distal tip 114 which is attached to the distal end of the inner body 116 to the target site within the epidural space. As shown below in FIGS. 7-9, the outer body 112 includes a lumen that the inner body 114 resides and moves within during the clearing process within the epidural space 108. The inner body 114 has a stiffness sufficient to allow the distal tip 114 to be effectively fed to the target site.

The inner body 114 may be formed as a tightly wound coil from a material such as stainless steel to allow such stiffness while also allowing for deflection within the lumen of the outer body 112 during insertion of the outer body 112 into the epidural space 108. The outer body 112 of the clearing tool 110 either has a pre-established deflection near the distal end or has a significant amount of flexibility to allow the outer body 112 to deflect when entering the epidural space.

The outer body 112 may be constructed of various materials to provide such malleability or flexibility. Examples of such materials to provide malleability include annealed stainless steel, platinum, or tantalum. Examples of such materials to provide flexibility include nylon, high density polyethylene, or polypropylene. To aid the clearing process for a flexible outer body 112, the outer body 112 of the tool 110 may also be made radiopaque by including materials such as tungsten, barium sulfate, and/or gold so as to be visible during fluoroscopy. Furthermore, these same materials may be applied to the distal tip so that the distal tip is also visible even when being extended to the target site.

Where the outer body 112 of the clearing tool 110 is flexible, the outer body 112 may have stiffness that increases in the proximal direction from the distal end but remains small enough in the distal region to not hinder deflection near the window 106. The increasing stiffness in the more proximal area of the outer body 112 aids in the insertion and clearing process by avoiding deflection in the more proximal region upon encountering obstructions at the distal end that creates backpressure upon the more proximal region of the outer body 112. For instance, the more proximal region of the outer body 112 may include an inner structure such as a metal braid or a metal coil that allows for increased stiffness. Another example is that this more proximal region is constructed from a material having a different durometer value from the distal region of the outer body 112 to provide the added stiffness in the more proximal region.

Figure 4:
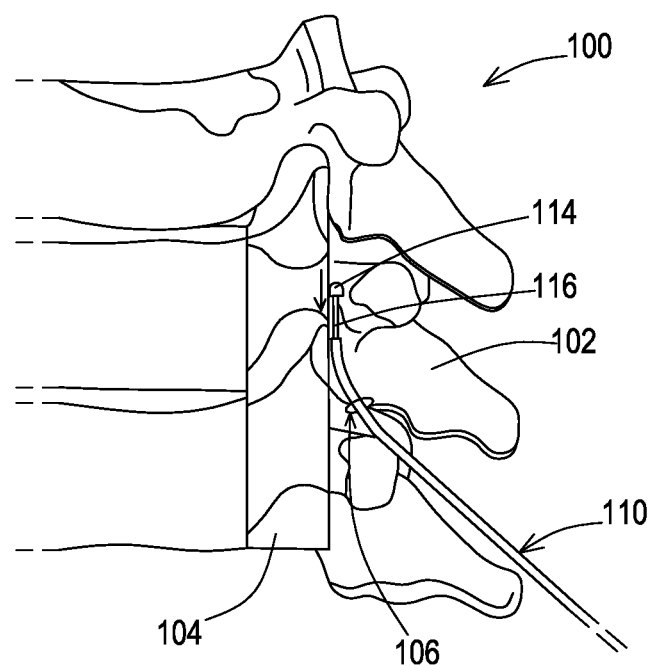
FIG. 4 shows the clearing tool transitioning back to the retracted state within the epidural space.

The inner body 116 is extended until the distal tip 114 of the clearing tool 110 has reached or exceeded the target site of stimulation within the epidural space 108. At that point, the inner body 116 may be retracted to further clear the epidural space 108 on the exit route back to the distal end of the outer body 112. The retraction of the inner body 116 is shown in FIG. 4. While the inner body 116 is being retracted, the outer body 112 of the clearing tool 110 remains in the fixed position.

Figure 5:
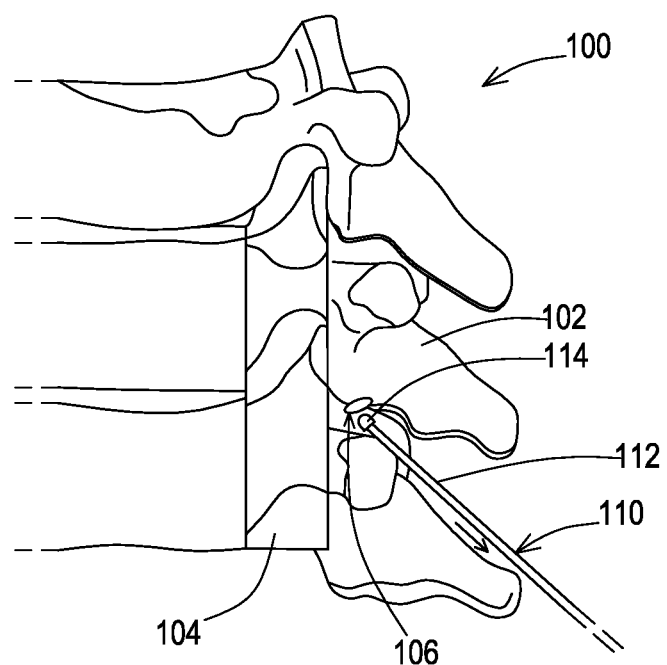
FIG. 5 shows the clearing tool in the retracted state while being removed from the epidural space.

At that point, the clearing tool 110 may be retracted back through the window 106. The retraction of the clearing tool 110 is shown in FIG. 5. While the clearing tool 110 is being retracted, the outer body 112 of the clearing tool 110 continues to deflect within the epidural space 108 in proximity to the window 106 to direct the clearing tool 110 out through the window 106 while continuing to avoid undue pressure on the dura 104.

Figure 6:
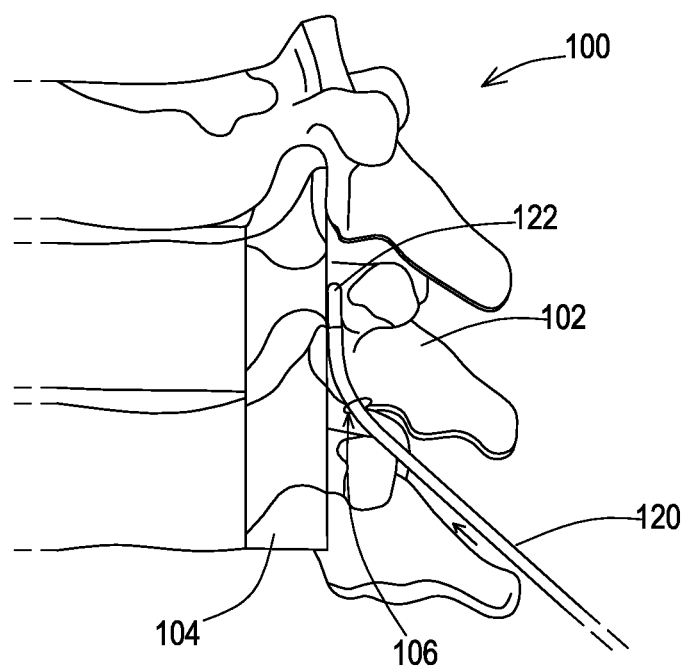
FIG. 6 shows the insertion of a medical lead into the cleared epidural space.

Once the clearing tool 114 has been removed from the spinal region 100, the medical lead 120 is then inserted through the window 106 and into the epidural space 108 as shown in FIG. 6. The medical lead 120 continues to be inserted until a distal end 122 such as a paddle of the medical lead 120 reaches the target stimulation site along the axial dimension of the dura 104. Afterward, the medical lead 120 is connected to a medical device that delivers the electrical stimulation signals that are output through electrodes in the distal end of the medical lead 120. As shown in FIG. 6, the body of the medical lead 120 may exceed that of the outer body 112 of the clearing tool 110, but the width of the distal tip 114 of the tool 110 has cleared the epidural space 108 so that the additional width of the medical lead 120 and the distal end 122 are not blocked during ingress by obstructions.

Figure 7:
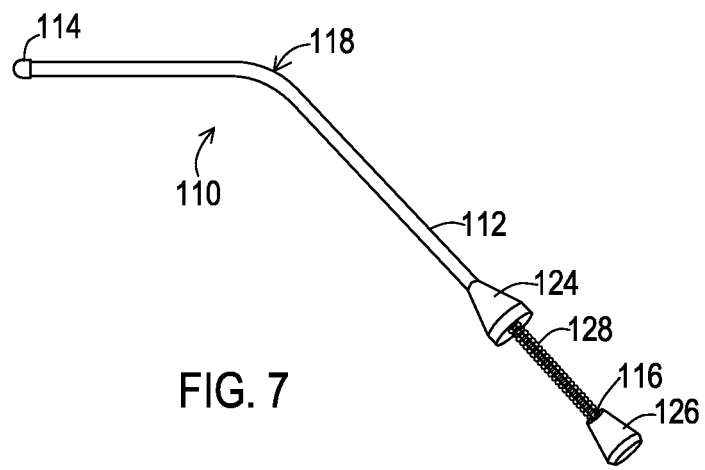
FIG. 7 shows an example of a clearing tool biased into the retracted state by a proximal spring.

An example of the clearing tool 110 is further shown in FIG. 7 while in the retracted state. Here, the proximal end of this example of the clearing tool 110 is also visible. The outer body 112 terminates at a hub 124 while the inner body 116 extends outwardly from a proximal end of the lumen of the outer body 112. The inner body 116 terminates at another hub 126. A surgeon using the clearing tool 110 to clear the epidural space may grasp the hub 124 with one hand and the hub 126 with the other to hold the outer body 112 in the fixed position within the epidural space 108 while moving the inner body 116 into the extended state and then back to the retracted state.

To ensure that the clearing tool 110 is in the retracted state during insertion into and removal from the epidural space 108, the clearing tool 110 may also include a biasing member such as a spring 128. In this example, the spring 128 is present between the hub 124 and the hub 126. The spring 128 biases the hub 126 proximally relative to the hub 124 which effectively maintains the inner body 116 in the retracted position. The surgeon then applies force to the hub 126 to oppose the bias of the spring 128 to thereby extend the inner body 116 from the lumen of the outer body 112.

Figure 8:
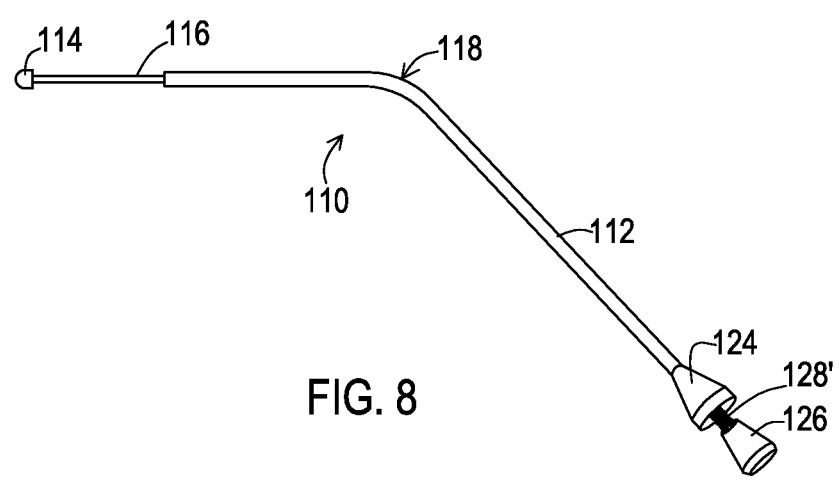
FIG. 8 shows the example of the clearing tool while being forced into the extended state in opposition to the bias from the spring.

FIG. 8 shows this example of the clearing tool 110 in the extended state once the force is being applied to the hub 126. The spring 128' is in the compressed state while the distal end of the inner body 116 has emerged from the distal end of the outer body 112. By decreasing the force being applied to the hub 126, the spring 128' then forces the inner body 116 to retract back into the outer body 112 and regain the retracted state shown in FIG. 7.

Figure 9:
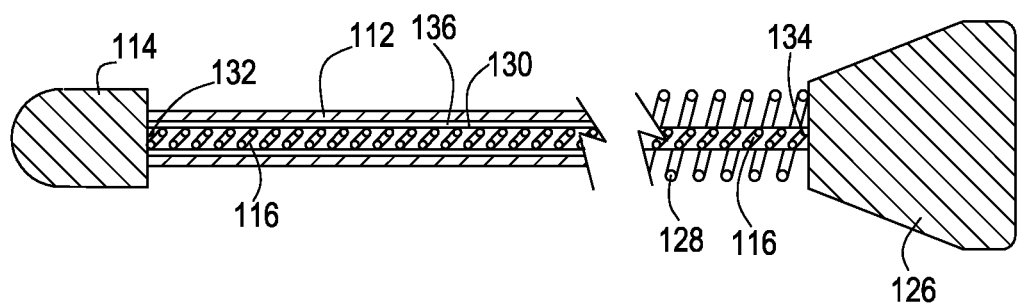
FIG. 9 shows a longitudinal cross-sectional view of an example of the clearing tool.

Embodiments of the clearing tool 110 may include various additional features. For instance, the distal tip 114 may be available in different sizes to provide clearing for different sizes of medical leads 120. Furthermore, for a given clearing tool 110, the distal tip 114 may be interchanged with distal tips of other sizes. One example of interchangeability is provided by having the distal tip 114 detach from the inner body 116. For instance, the distal tip 114 may have eccentrically aligned and axially spaced rings that surround and catch upon the inner body 116, for instance on a small section of the inner body 116 with increased diameter of purposes of retaining the rings. These rings of the distal tip 114 may then release from the inner body 116 upon inward pressure being applied to the distal tip 114 to force the rings into a concentric relationship that allows the distal tip 114 to slide distally off of the inner body 116. FIG. 9 shows a longitudinal cross-sectional view of an example of the clearing tool 110. In this example, the inner body 116 is in the form of a coil present within the lumen 136 of the outer body 112. When retracting the inner body 116 from its fully extended state, the distal tip 114 as well as the inner body 116 itself may continue to encounter obstacles within the epidural space 108 and clear those obstacles.

However, while retracting the inner body 116, the inner body 116 and/or distal tip 114 may continue to encounter an obstacles within the epidural space which are being cleared. The tendency may be for the coil forming the inner body 116 to attempt to elongate while being retracted due to encountering the obstacles that remain. To prevent such elongation, a ribbon 130 may be included. The ribbon 130 may have an attachment 132 near a distal end of the inner body 116 as well as an attachment 134 near a proximal end. The ribbon 130 thereby limits the distance between the proximal end and distal end of the inner body 116 such that the inner body 116 cannot elongated while being retracted. The ribbon 130 may be constructed of a material such as stainless steel.

While embodiments have been particularly shown and described, it will be understood by those skilled in the art that various other changes in the form and details may be made therein without departing from the spirit and scope of the invention.

What is claimed is:

1. A clearing tool for clearing an epidural space in preparation for implantation of a medical lead within the epidural space, comprising:
   an outer body with a lumen having a distal end and a proximal end, the outer body being an outermost body of the clearing tool;
   an inner body within the lumen, the inner body being movable in an axial direction within the lumen relative to the outer body between an extended and a retracted state, a proximal end of the inner body residing proximal to the proximal end of the outer body at least when the inner body is in the retracted state and a distal end of the inner body residing distal to the distal end of the outer body at least when the inner body is in the extended state, the inner body being an innermost body of the clearing tool;
   a distal tip affixed to a distal end of the inner body and residing distally of the lumen at least when the inner body is in the extended state, the distal tip having a greater diameter than the inner body, the distal tip having eccentrically aligned and axially spaced rings that surround and catch upon the inner body, where a small section of the inner body with increased diameter retains the rings that release from the inner body upon inward pressure being applied to the distal tip to force the rings into a concentric relationship that allows the distal tip to slide distally off of the inner body; and
   a spring located between the hub of the inner body and the hub of the outer body to contact the hub of the inner body and the hub of the outer body to bias the inner body into the retracted state.

2. The clearing tool of claim 1, wherein the outer body is malleable.

3. The clearing tool of claim 1, wherein the outer body is flexible.

4. The clearing tool of claim 1, wherein the inner body is a coil.

5. The clearing tool of claim 4, further comprising a ribbon attached to a distal end and a proximal end of the coil.

* * * * *